United States Patent [19]

Capuzzi et al.

[11] Patent Number: 5,238,957
[45] Date of Patent: Aug. 24, 1993

[54] ESTERS OF 2,2-DIMETHYL-CYCLOPROPANE-CAR-BOXYLIC ACID

[75] Inventors: Luigi Capuzzi; Franco Bettarini, both of Novara; Paolo Castoro, Vercelli; Sergio Massimini, Milan; Vincenzo Caprioli, San Martino Siccomario, all of Italy

[73] Assignee: Presidenza Del Consiglio Dei Ministri-Uffico del Ministro per il coordinamento delle Iniziative per la ricerca Scientifica e Tecnologica, Rome, Italy

[21] Appl. No.: 961,030

[22] Filed: Oct. 14, 1992

Related U.S. Application Data

[63] Continuation of Ser. No. 778,755, Oct. 18, 1991, abandoned, which is a continuation of Ser. No. 607,639, Oct. 31, 1990, abandoned, which is a continuation of Ser. No. 376,564, Jul. 7, 1989, abandoned.

[30] Foreign Application Priority Data

Jul. 7, 1988 [IT] Italy ............... 21268 A/88

[51] Int. Cl.⁵ .................................... A01N 53/00
[52] U.S. Cl. ........................... 514/531; 560/124; 549/479; 549/501
[58] Field of Search ............. 560/124; 514/531

[56] References Cited

U.S. PATENT DOCUMENTS

| | | | |
|---|---|---|---|
| 4,237,126 | 12/1980 | Roman | 560/124 |
| 4,252,820 | 2/1981 | Lantzsch | 560/124 |
| 4,256,907 | 3/1981 | Naumann | 560/124 |
| 4,285,969 | 8/1981 | Galli | 560/124 |
| 4,299,839 | 11/1981 | Omura | 560/124 |
| 4,327,109 | 4/1982 | Mizutani | 560/124 |
| 4,328,237 | 5/1982 | Piccardi | 560/124 |
| 4,332,815 | 6/1982 | Engel | 560/124 |
| 4,401,673 | 8/1983 | Martel | 560/124 |
| 4,551,546 | 11/1985 | Punja | 560/124 |
| 4,582,856 | 4/1986 | Lantzsch | 560/124 |
| 4,622,337 | 11/1986 | Elliott | 560/124 |
| 4,902,697 | 2/1990 | Capuzzi | 560/124 |

FOREIGN PATENT DOCUMENTS 258815  3/1988  European Pat. Off. ............ 560/124

OTHER PUBLICATIONS

Elliott, Chem. Soc. Rev., 7, pp. 473–505 (1978).

Primary Examiner—Michael L. Shippen
Attorney, Agent, or Firm—Stevens, Davis, Miller & Mosher

[57] ABSTRACT

New esters of 2,2-dimethyl-cyclopropane-carboxylic acid, which are endowed with insecticidal and acaricidal activity, have the general formula:

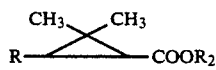

wherein:
represents

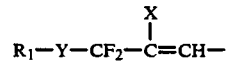

or a

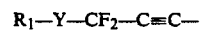

group;
Y represents either O or S;
X represents H, F, Cl, Br, or —CF₃;
$R_1$ represents either a linear or a branched ($C_1$–$C_6$)-aklyl group, or a ($C_3$–$C_6$)-cycloalkyl group, optionally substituted with halogen atoms;
$R_2$ represents one from the following groups:

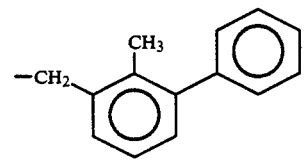

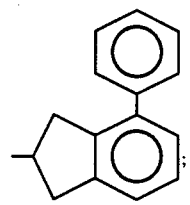

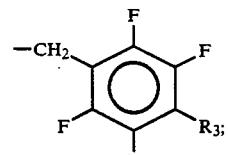

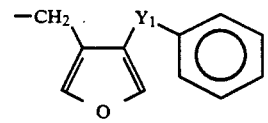

wherein:
$R_3$ represents an F atom, a ($C_1$–$C_5$)-aklyl, an alkyloxy, an alkylthio, an alkylsulfinyl, or an alkylsulfonyl group; and
$Y_1$ is either O or CH₂.

8 Claims, No Drawings

ESTERS OF 2,2-DIMETHYL-CYCLOPROPANE-CARBOXYLIC ACID

This application is a continuation of application Ser. No. 07/778,755, filed Oct. 18, 1991, now abandoned, which in turn is a continuation of application Ser. No. 07/607,639, filed Oct. 31, 1990, now abandoned, which in turn is a continuation of application Ser. No. 376,564, filed Jul, 7, 1989, now abandoned.

DESCRIPTION OF THE INVENTION

The present invention relates to new esters endowed with insecticidal and acaricidal activity, derived from 2,2dimethyl-cyclopropane-carboxylic acid (synthetic pyrethroids), to the process for preparing them, to insecticidal and acaricidal compositions containing the new esters, and to the use of said compositions in order to control insects and acari.

Several compositions belonging to the class of the synthetic pyrethroids are known, which are used in the fight against noxious insects both in the agricultural and in civilian fields. Among these, the most important compounds are the derivatives of 2,2dimethyl-cyclopropane-carboxylic acid, such as, e.g., permethrin, cypermethrin and deltamethrin ("Synthesis Pyrethroids," A.C.S. Symposium Series 42, 1977), and those such as are disclosed in European patent application No. 258,815.

An important limitation of the presently marketed products, in particular the products derived from α-cyanophenoxy-benzyl alcohol, is that they are considerably toxic against useful insects (such as bees and predator insects) and for other animal organisms (in particular, for fishes).

In accordance with the present invention, it has now been discovered that new ester derivatives of 2,2-dimethyl-cyclopropane-carboxylic acid, endowed with a high insecticidal and acaricidal activity as regards some noxious species, which at the same time turn out to be only slightly toxic against useful insects and higher animals.

Therefore, an object of the present invention is to provide new esters of 2,2-dimethyl-cyclopropane-carboxylic acid, having the formula (I):

$$\text{R}\overset{\text{CH}_3\quad\text{CH}_3}{\triangle}\text{COOR}_2$$

wherein:
R represents s

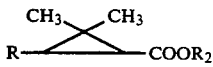

or a

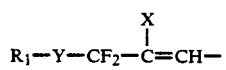

group;
Y represents either O or S;
X represents H, F, Cl, Br, or —CF$_3$;
R$_1$ represents either a linear or a branched (C$_1$–C$_6$)-alkyl group, or a (C$_3$–C$_6$)-cycloalkyl group, optionally substituted with halogen atoms;
R$_2$ represents one from the following groups:

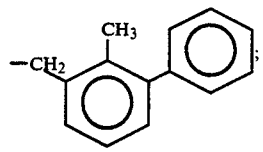

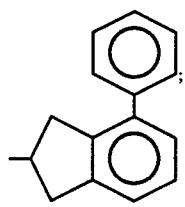

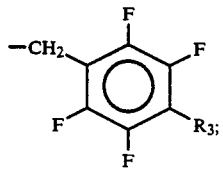

and

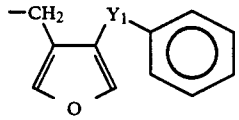

wherein:
R$_3$ represents an F atom, a (C$_1$–C$_5$)-aklyl, an alkyloxy, an alkylthio, an alkylsulfinyl, or an alkylsulfonyl group; and
Y$_1$ is either O or CH$_2$.

Preferably, R$_1$ represents a (C$_1$–C$_6$)-alkyl group, or a (C$_3$–C$_6$)-cycloalkyl group, substituted with at least one fluorine atom.

Such compounds are endowed with a high insecticidal and acaricidical activity against a large number of species of harmful insects in the agricultural and civilian fields, belonging to the classes of Hemiptera, Lepidoptera, Coleoptera, Diptera, Blattidae, and Tetranydae, while at the same time they are not very toxic toward important useful insects (such as bees, and so on), and for higher animals (such as mammals, fishes and birds).

The preparation of the compounds of formula (I) is carried out by the esterification of a carboyxylic acid or of an acyl derivative thereof, having the formula (II):

$$\text{R}\overset{\text{CH}_3\quad\text{CH}_3}{\triangle}\text{COOR}_4 \qquad (II)$$

wherein:
R has the above detailed meaning; and
R$_4$ represents H, Cl, or an (C$_1$–C$_4$)-aklyl with an alcohol of the formula:

R$_2$—OH wherein R$_2$ has the same meaning as stated above as regards formula (I).

The reaction of esterification may be carried out according to various techniques, all falling within the scope of normal procedure in organic chemistry.

Preferably, an acid of formula (II) (with $R_4$=H) is converted into its acyl chloride with a suitable agent, such as, e.g., oxylyl chloride, thionyl chloride, phosphorus pentachloride, and so forth, in an inert solvent at a temperature within the range of from room temperature up to the solvent-refluxing temperature, and is then reacted with one equivalent of an alcohol of formula:

$$R_2\text{—OH}$$

in an inert anhydrous organic solvent at room temperature in the presence of an organic base, preferably constituted by a tertiary amine, such as pyridine or triethylamine.

The alcohols of formula $R_2$—OH are known compounds.

The compounds of the formula (II), wherein
$R = R_1$—Y—$CF_2$—C(X)=CH— and
X=F, Cl, Br, $CF_3$,
may be prepared by starting from polyfluorohalogenated ethers of formula (III)

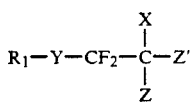
(III)

wherein $R_1$, X and Y have the same meanings as reported above in the formula (I), and Z and Z', which may be the same, or different from each other, are Br or Cl atom (in particular when X=Cl).

The compounds of formula (III) are known products, or they may anyway be obtained by processes described in the relevant technical literature, such as, e.g., in Angew. Chem. Int. Ed. Engl. 24(1985) 871; in U.S. Pat. No. 3,388,078 (C.A. 69:28654a); and in J. Org. Chem. 50 (1985), 4047-4051.

Compounds of the formula (II) may be efficaciously prepared by one of the following methods:

"A" Method

By means of a procedure similar to that described, e.g., in DOS 2,539,895 (1976) and Bull. Chem. Soc. Jpn. 52, 1511 (1979), a compound of formula (III) is added to the ethyl ester of 3,3-dimethyl-4-pentenoic acid in the presence of a suitable promoter of radicalic reactions (1A step); the so-obtained adduct is cyclized (2A step) and is furthermore dehydrohalogenated (3A step) by treatment with a base in order to yield a compound of the formula (II) wherein
$R_4 = C_2H_5$ and $$R = R_1\text{—Y—}CF_2\text{—C=CH— (III) +}$$
$$\phantom{R = R_1\text{—Y—}CF_2\text{—}}|$$
$$\phantom{R = R_1\text{—Y—}CF_2\text{—}}X$$

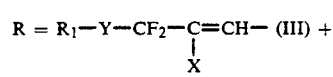

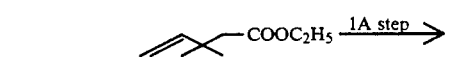

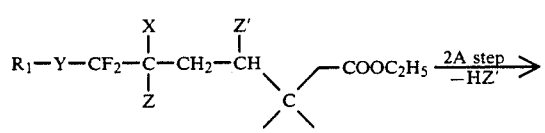

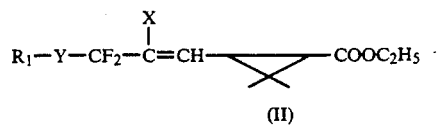
(II)

"B" Method

In an analogous way to that disclosed in European patent application No. 187,674, a compound of formula (III) is reacted with caronaldehyde (ethyl 2,2-dimethyl-3-formylcyclopropanecarboxylate) in the presence of such metals as zinc or magnesium (1B step); by the subsequent dehydroxyhalogenation of the carbinal thus obtained of formula (IV)—e.g., by acetylation and subsequent treatment with Zn (2B step)—a compound of the formula (II) is obtained wherein
$R_2 = C_2H_5$ and $$R = R_1\text{—Y—}CF_2\text{—C=CH—: (III) +}$$
$$\phantom{R = R_1\text{—Y—}CF_2\text{—}}|$$
$$\phantom{R = R_1\text{—Y—}CF_2\text{—}}X$$

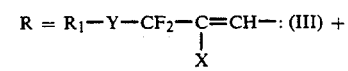

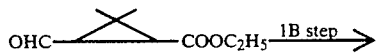

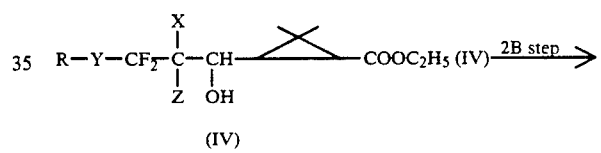
(IV)

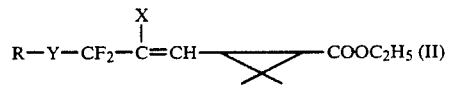

"C" Method

As an alternative, compounds having the formula (II) wherein
$R = R_1$—Y—$CF_2$—C(X)=CH— and
X=F, Cl, Br, $CF_3$
may be prepared by reacting a metal salt of formula:

$$R_1Y^-M^+ \qquad\qquad\text{(IV)}$$

with a difluoroolefin of formula (V):

according to the following reaction scheme:

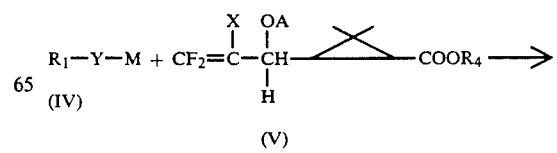

-continued

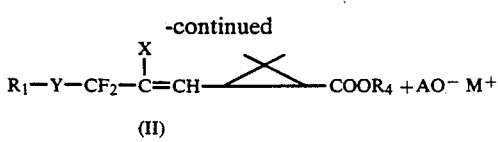

(II)

wherein:
R₁, Y, X, R₄ have the same meanings as defined above,
M is an alkali metal selected from the group consisting of K, Li, Na, and
A represents H or an acyl or a sulfonic group preferably selected from among CH₃CO, CH₃SO₂, CF₃SO₂, CH₃—C₆H₆—CO₂.

"D" Method

Compounds having the formula (II) in which
R=R₁—Y—CF₂—C≡C—
may e prepared by the dehydrochlorination of compounds of the formula (II) in which:
R=R₁—Y—CF₃—C(X)=CH—, and
X=Cl or Br,
according to the following method:

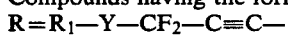

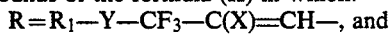

wherein the various symbols have the same meanings as defined above.

The dehydrochlorination may be carried out according to various techniques as described in the relevant technical literature and is preferably carried out by treating the initial product with a strong base such as NaOH, KOH, NaNH₂, tert.-BuOK, in an aprotic dipolar solvent at a temperature preferably within the range of from 40° C. up to about 100° C.

"E" Method

Compound of the formula (II) wherein X=H may be prepared by hydrogenation of the corresponding propargyl derivatives of formula (II), with R=R₁—Y—CF₂—C≡C—
according to traditional methods of catalytic hydrogenation:

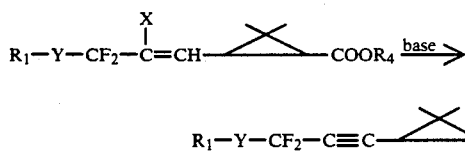

The compounds of formula (I) may be in the form of isomeric mixtures.

The separation of the mixture into their components may be carried out by using known chemical techniques, such as column chromatography or thin-layer chromatography.

The isolation and the use of each steric and/or configurational isomers, as well as the direct use of the mixtures which may be obtained from the preparation of the compounds, and the use of the mixtures deriving from an incomplete separation of the isomers are all contemplated as being within the scope of the present invention.

As mentioned above, the compounds of formula (I) are endowed with a high insecticidal activity.

They are characterized by a wide spectrum of action against insects belonging to several families, such as Hemiptera, Lepidoptera, Diptera, Coleoptera, Aphids, and so forth, and they furthermore also display a satisfactory acaricidal activity.

Thanks to their positive characteristics, the compounds of formula (I) are well suited for use in the defense of cultivations of agrarian interest, and in the meantime in the defense from noxious insects of sites hunted by man and by domestic animals and especially breeding livestock.

For the purposes of their practical use, both in agriculture and in other use sectors, the compounds according to the present invention are advantageously used in the form of suitable compositions.

These compositions contain, besides one or more compound(s) of formula (I) as their active principle, inert solid carriers (such as, e.g., kaolin, silica, talc, attapulgite, diatomaceous earth, and so forth), or inert liquid carriers (organic solvents, vegetable or mineral oils, water and their mixtures) and if desired still other additives which are normally used in the preparation of such formulations, such as surfactants, suspending agents, dispersants, and wetting agents.

For particular application requirements, or in order to expand the action spectrum of the compositions, to the above described compositions still other active ingredients may be added such as, e.g., other insecticides or acaricides, herbicides, fungicides or fertilizers.

The application doses vary as a function of several factors, such as the type and the level of infestation, the type of composition used, and climatic and environmental factors.

For practical use in agriculture, doses of compound of formula (I) within the range of from 10 to 500 g/ha yield satisfactory results.

The following examples are supplied in order still better to illustrate the invention, but without limitation on the scope thereof.

EXAMPLE 1

Synthesis of 2-methyl-3-phenyl-benzyl cis-2,2-dimethyl-3-[2-chloro-2-(2,2,2-trifluoroethoxy)-difluoromethyl]-vinyl-cyclopropane-carboxylate 1.98 g (10 mmol) of 2-methyl-3-phenyl-benzyl alcohol, 10 ml of anhydrous ether, 1 ml of pyridine, and 3.4 g (10 mmol) of cis-2,2-dimethyl-3-[2-chloro-2-(2,2,2-trifluoroethoxy)-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off and the filtrate is washed with HCl at 1%, with bicarbonate and with brine. The filtrate is then thoroughly dried and is concentrated to dryness. A raw oil (4.8 g) is obtained, which is chromatographed on silica gel, with 99:1 hexane/ethyl acetate as the eluent, 3.5 g of pure product is obtained.

NMR (60 MHz, CDCl₃): δ 1.25 s.6H; 2.2 s.3H; 2.35–1.9 m.2H; 4.15 q.(J=8Hz)2H; 5.10 s.2H; 6.8 d.(J=3Hz), 7.4–7.05 m.8H.

EXAMPLE 2

Synthesis of 2-methyl-3-phenyl-benzyl trans-2,2-dimethyl-3-[2-chloro-2-(2,2,2-trifluoroethyoxy)-difluoromethyl]-vinyl-cyclopropane-carboxylate 1.98 g (10 mmol) of 2-methyl-3-phenyl-benzyl alcohol, 15 ml of anhydrous ether, 1 ml of pyridine, and 3.4 g (10 mmol) of trans-2,2-dimethyl-3-[2-chloro-2-(2,2,2-trifluoroethyoxy)-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off and the filtrate is washed with HCl at 1%, with bicarbonte and with brine. The filtrate is then thoroughly dried and is concentrated to dryness. A raw oil (4.5 g) is obtained, which is chromatographed on silica gel, with 99:1 hexane/ethyl acetate as the eluent. 3.69 g of pure product is obtained.

NMR (60 MHz, CDCl$_3$): δ 1.15 s.3H; 1.25 s.3H; 1.68 q.(J=6Hz)1H; 2.12 s.3H; 2.4–2.1 m.1H; 4.1 q.(J=8Hz)2H; 5.05 s.2H; 5.99 d.(J=8Hz), 7.3–6.9 m.8H.

EXAMPLE 3

Synthesis of pentafluorobenzyl cis-2,2-dimethyl-3-[2-chloro-2-(2,2,2-trifluoroethoxy)-difluoromethyl]-vinyl-cyclopropane-carboxylate 0.99 g (5 mmol) of pentafluoro-benzyl alcohol, 5 ml of anhydrous ether, 1 ml of pyridine, and 1.7 g (5 mmol) of cis-2,2-dimethyl-3-[2-chloro-2-(2,2,2-trifluoroethoxy)-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off and the filtrate is washed with HCl at 1%, with bicarbonate and with brine. The filtrate is then thoroughly dried and is concentrated to dryness. A raw oil (2.48 g) is obtained, which is chromatographed on silica gel, with 99:1 hexane/ethyl acetate as the eluent. 1.99 g of pure product is obtained.

NMR (60 MHz, CDCl$_3$): δ 1.3 s.6H; 2.4–1.8 m. 2H; 4.2 q.(J=8.5Hz)2H; 5.1 s.2H; 7.1–6.6 m.1H.

EXAMPLE 4

Synthesis of 2,3,5,6-tetrafluoro-4-methyl-benzyl trans-2,2-dimethyl-3-[2-chloro-2-(2,2,2-trifluoroethyoxy)-difluoromethyl]-vinyl-cyclopropane-carboxylate 0.97 g (5 mmol) of 2,3,5,6-tetrafluoro-4-methyl-benzyl alcohol, 5 ml of anhydrous ether, 1 ml of pyridine, and 1.7 g (5 mmol) of trans-2,2-dimethyl-3-[2-chloro-2-(2,2,2-trifluoroethyoxy)-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off and the filtrate is washed with HCl at 1%, with bicarbonate and with brine. The filtrate is then thoroughly dried and is concentrated to dryness. A raw oil (2.58 g) is obtained, which is chromatographed on silica gel, with 99:1 hexane/ethyl acetate as the eluent. 1.69 g of pure product is obtained.

NMR (60 MHz, CDCl$_3$): δ 1.1 s.3H; 1.2 s.3H; 1.62 d.(J=6Hz)1H; 2.1 s.3H; 2.4–2.0 m.1H; 4.1 q.(J=8Hz)2H; 5.1 s.2H; 6.0 d.(J=8Hz)1H.

EXAMPLE 5

Synthesis of 2-methyl-3-phenyl-benzyl trans-z-2,2-dimethyl-3-[2-(2,2,2-trifluoroethyoxy)-difluoromethyl]-vinyl-cyclopropane-carboxylate 1.98 g (10 mmol) of 2-methyl-3-phenyl-benzyl alcohol, 5 ml of anhydrous ether, 1 ml of pyridine, and 3.07 g (5 mmol) of trans-z-2,2-dimethyl-3-[2-(2,2,2-trifluoroethyoxy)-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off and the filtrate is washed with HCl at 1%, with bicarbonate and with brine. The filtrate is then thoroughly dried and is concentrated to dryness. A raw oil (4.65 g) is obtained, which is chromatographed on silica gel, with 99:1 hexane/ethyl acetate as the eluent. 3.46 g of pure product is obtained.

NMR (60 MHz, CDCl$_3$): δ 1.12 s.3H; 1.22 s.3H; 1.65 d.(J=5Hz)1H; 2.15 s.3H; 2.7–2.3 m.1H; 4.1 q.(J=8.5Hz)2H; 5.11 s.2H; 5.7–5.4 m2H;7.4–7 m.8H.

EXAMPLE 6

Synthesis of 2-methyl-3-phenyl-benzyl trans-2,2-dimethyl-3-[2-chloro-2-(2,2,3,3-tetrafluoropropoxy)-difluoromethyl]-vinyl-cyclopropane-carboxylate 0.99 g (5 mmol) of 2-methyl-3-phenyl-benzyl alcohol, 10 ml of anhydrous ether, 1 ml of pyridine, and 1.86 g (5 mmol) of trans-2,2-dimethyl-3-[2-chloro-2-(2,2,3,3-trifluoropropoxy)-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off the filtrate is washed with HCl at 1%, with bicarbonate and with brine. The filtrate is then thoroughly dried and is concentrated to dryness. A raw oil (2.49 g) is obtained, which is chromatographed on silica gel, with 99:1 hexane/ethyl acetate as the eluent. 1.88 g of pure product is obtained.

NMR (60 MHz, CDCl$_3$): δ 1.12 s.3H; 1.27 s.3H; 1.74 d.(J=5Hz)1H; 2.15 s.3H; 2.37 d.d(J$_1$=9Hz, J$_2$=5Hz)1H; 4.15 t.(J=12Hz)2H; 5.15 s.2h; 5.75 t.t.(J$_1$53Hz, J$_2$=4Hz); 6.02 d.(J=9Hz)1H; 7.3–7.05 m.8H.

EXAMPLE 7

Synthesis of pentafluoro-benzyl trans-2,2-dimethyl-3-[2-chloro-2-(2,2,3,3-tetrafluoropropoxy)-difluoromethyl]-vinyl-cyclopropane-carboxylate 0.99 g (5 mmol) of pentafluoro-benzyl alcohol, 10 ml of anhydrous ether, 1 ml of pyridine, and 1.86 g (5 mmol) of trans-2,2-dimethyl-3-[2-chloro-(2,2,3,3-tetrafluoropropoxy)-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off the filtrate is washed with HCl at 1%, with bicarbonate and with brine. The filtrate is then thoroughly dried and is concentrated to dryness. A raw oil (2.59 g) is obtained, which is chromatographed on silica gel, with 99:1 hexane/ethyl acetate as the eluent. 2.05 g of pure product is obtained.

NMR (60 MHz, CDCl$_3$): δ 1.1 s.3H; 1.2 s.3H; 1.62 d.(J=6Hz)1H; 2.25 d.d(J$_1$=6Hz; J$_2$=8Hz)1H; 4.10 t.(J=12Hz)2H; 5.05 s.2H; 5.75 t.t.(J$_1$=4Hz, J$_2$=52Hz);1H.

EXAMPLE 8

Synthesis of 2,3,5,6-tetrafluoro-4-methyl-benzyl trans-2,2-dimethyl-3-[2-chloro-2-(2,2,3,3-tetrafluoropropoxy)-difluoromethyl]-vinyl-cyclopropane-carboxylate 0.97 g (5 mmol) of 2,3,5,6-tetrafluoro-4-methyl-benzyl, 10 ml of anhydrous ether, 1 ml of pyridine, and 1.86 g (5 mmol) of trans-2,2-dimethyl-3-[2-chloro-(2,2,3,3-tetrafluoropropoxy)-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off the filtrate is washed with HCl at 1%, with bicarbonate and with brine. The filtrate is then thoroughly dried and is concentrated to dryness. A raw oil (2.51 g) is obtained, which is chromatographed on silica gel, with 99:1 hexane/ethyl acetate as the eluent. 2 g of pure product is obtained.

NMR (60 MHz, CDCl$_3$): δ 1.1 s.3H; 1.2 s.3H; 1.65 d.(J=6Hz)1H; 2.1 s.3H; 2.4–2.0 m.1H; 4.15 t.(J=12Hz)2H; 5.1 s.2H; 5.8 t.t.(J$_1$=4Hz, J$_2$=52Hz);1H; 6.0 d.(J=8Hz)1H.

EXAMPLE 9

Synthesis of 2-methyl-3-phenyl-benzyl trans-2,2-dimethyl-3-[2-chloro-2-methoxy-difluoromethyl]-vinyl-cyclopropane-carboxylate 1.98 g (10 mmol) of 2-methyl-3-phenyl-benzyl alcohol, 15 ml of anhydrous ether, 1 ml of pyridine, and 2.73 g (10 mmol) of trans-2,2-dimethyl-3-[2-chloro-2-methoxy-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off the filtrate is washed with HCl at 1%, with bicarbonate and with brine. The filtrate is then thoroughly dried and is concentrated to dryness. A raw oil (4.58 g) is obtained, which is chromatographed on silica gel, with 99:1 hexane/ethyl acetate as the eluent. 3.69 g of pure product is obtained.

NMR (60 MHz, CDCl$_3$): δ 1.2 s.6H; 1.67 d.(J=6Hz)1H; 2.12 s.3H; 2.4–1.9 m.1H; 3.5 s.3H; 5.05 s.2H; 6.0 d (J=8Hz)1H; 7.3–7.0 m.8H.

EXAMPLE 10

Synthesis of pentafluorobenzyl trans-2,2-dimethyl-3-(2-chloro-2-methoxy-difluoromethyl)-vinyl-cyclopropane-carboxylate 0.99 g (5 mmol) of pentafluorobenzyl alcohol, 5 ml of anhydrous ether, 1 ml of pyridine, and 1.37 g (5 mmol) of trans-2,2-dimethyl-3-(2-chloro-(2-methoxy-difluoromethyl)-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off and the filtrate is washed with HCl at 1%, with bicarbonate and with brine. The filtrate is then thoroughly dried and is concentrated to dryness. A raw oil (2.08 g) is obtained, which is chromatographed on silica gel, with 99:1 hexane/ethyl acetate as the eluent. 1.641 g of pure product is obtained.

NMR (60 MHz, CDCl$_3$): δ 1.1 s.3H; 1.2 s.3H; 1.65 d.(J=6Hz)1H; 2.3 d.d(J=9Hz, J$_2$=6Hz)1H; 3.5 s.3H; 5.1 s.2H; 5.98 d. (J=9Hz)1H.

EXAMPLE 11

Synthesis of 2,3,5,6-tetrafluoro-4-methyl-benzyl trans-2,2-dimethyl-3-(2-chloro-2-methoxy-difluoromethyl)-vinyl-cyclopropane-carboxylate 0.97 g (5 mmol) of 2,3,5,6-tetrafluoro-4-methyl-benzyl alcohol, 5 ml of anhydrous ether, 1 ml of pyridine, and 1.37 g of trans-2,2-dimethyl-3-(2-chloro-2-methoxy-difluoromethyl)-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off and the filtrate is washed with HCl at 1%, with bicarbonate and with brine. The filtrate is then thoroughly dried and is concentrated to dryness. A raw oil (2 g) is obtained, which is chromatographed on silica gel, with 99:1 hexane/ethyl acetate as the eluent. 1.60 g of pure product is obtained.

NMR (60 MHz, CDCl$_3$): δ 1.1 s.3H; 1.2 s.3H; 1.65 d.(J=6Hz)1H; 2.1 s.3H; 2.4–2.0 m.1H; 3.5 s.3H; 5.1 s.2H; 6.0 d.(J=9Hz)1H.

EXAMPLE 12

Synthesis of 2-methyl-3-phenyl-benzyl trans-2,2-dimethyl-3-[2-chloro-2-(2,2,3,3,3-pentafluoropropoxy)-difluoromethyl]-vinyl-cyclopropane-carboxylate 0.99 g (5 mmol) of 2-methyl-3-phenyl-benzyl alcohol, 10 ml of anhydrous ether, 1 ml of pyridine, and 1.96 g (5 mmol) of trans-2,2-dimethyl-3-[2-chloro-2-(2,2,3,3,3-pentafluoropropoxy)-difluoromethyl]-vinyl-cyclopropane-carbonyl chloride are charged to a 50 ml 3-neck flask under a nitrogen blanketing atmosphere.

The reaction mixture is kept stirred for 3 hours at room temperature.

The precipitate is filtered off and the filtrate is washed with HCl at 1%, with bicarbonate and with brine. The filtrate is then thoroughly dried and is concentrated to dryness. A raw oil (2.72 g) is obtained, which is chromatographed on silica gel, with 99:1 hexane/ethyl acetate as the eluent. 2.17 g of pure product is obtained.

NMR (60 MHz, CDCl$_3$): δ 1.2 s.6H; 1.68 d.(J=6Hz)1H; 2.12 s.3H; 2.4–1.9 m.1H; 4.2 t.(J=12Hz)2H; 5.05 s.2h; 6.0 d.(J=8Hz)1H; 7.3–7 m.8H.

EXAMPLE 13

DETERMINATION OF THE INSECTICIDAL AND ACARICIDAL ACTIVITY

A. Insecticidal Activity Against *Macrosiphum euphorbiae* (aphids).

Potato plants grown in pot were infected with adult females of the aphid and some hours later on them a suspension in water-acetone (at 10% by volume of acetone) of the product under investigation was sprayed.

24 hours after the treatment, the % death-rate of the aphids was determined as compared to the death-rate of aphids infesting plants treated only with an aqueous solution at 10% of acetone.

B. Insecticidal Activity Against *Leptinotarsa decemylineata* (Coleoptera)

Potato plants grown in pot were infested with 4-day old larvae of the coleoptera.

Then a dispersion of water-acetone (at 10% by volume for acetone) of the product under investigation was sprayed onto the plants.

The % death-rate of the larvae was evaluated 48 hours after the treatment, as compared to the death-rate of larvae infesting plants treated only with an aqueous solution of acetone at 10%.

C. Insecticidal Activity Against *Aedes aegypti* (Diptera)

Four-days old larvae of this dipteral were transferred into vessels containing 300 ml of a solution in water-acetone (at 1% of acetone) of the product under investigation.

The % death-rate of the larvae was evaluated 48 hours after the treatment, as compared to the death-rate of larvae charged to an aqueous solution containing only 1% of acetone.

D. Insecticidal Activity Against *Tetranychus urticae*

Disks cut from leaves of beans were infested with adult acari and on them a solution in water-acetone (acetone at 10% by volume) of the product under investigation was sprayed.

The % death-rate was determined 24 hours after the treatment, as compared to the death-rate of acari infesting disks on which only an aqueous solution at 10% of acetone was sprayed.

By operating according to the above procedures, compounds according to the present invention were tested in order to determine their insecticidal and acaricidal activity.

The insecticidal activity was evaluated on the basis on the % death-rate at the different doses of active compound, and was expressed according to the following scale of values:

| | |
|---|---|
| 5 = Complete activity | Death-rate higher than 90% |
| 4 = High activity | Death-rate within the range of from 80 to 90% |
| 3 = Fairly good activity | Death-rate within the range of from 60 to 79% |
| 2 = Medium activity | Death-rate within the range of from 40 to 59% |
| 1 = Poor activity | Death-rate within the range of from 20 to 39% |
| 0 = Negligible activity | Death-rate within the range of from 0 to 19% |

The results of the determinations carried out are reported in Table 1.

TABLE 1

| Compound Example N | Eggs of Leptinotarsa | | Larvae of Aedes aegypti | | Adults of Macrosiphum euphorbiae | |
|---|---|---|---|---|---|---|
| 12 | 100 ppm | 5 | 0.02 ppm | 5 | | |
| 1 | 100 ppm | 5 | 0.02 ppm | 4 | | |
| 2 | 100 ppm | 5 | 0.02 ppm | 5 | 10 ppm | 5 |
| | 10 ppm | 3 | | | | |
| 3 | 100 ppm | 5 | 0.02 ppm | 5 | 10 ppm | 5 |
| | | | | | 1 ppm | 3 |
| 5 | 100 ppm | 5 | 0.02 ppm | 3 | 10 ppm | 5 |

What is claimed is:

1. A compound having the formula:

wherein R represents an

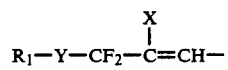

or

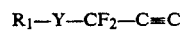

group;
Y represents O;
X represents Cl;
$R_1$ represents either a linear or branched ($C_1$–$C_6$)-aklyl group; substituted with halogen atoms; and
$R_2$ represents

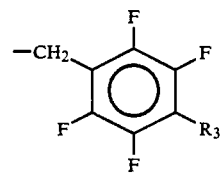

wherein $R_3$ represents an F atom and a ($C_1$–$C_5$)-aklyl group.

2. A compound according to claim 1, wherein $R_1$ is substituted with at least one fluorine atom.

3. A compound according to claim 1, which is pentafluorobenzyl cis-2,2-dimethyl-3-[2-chloro-2-(2,2,2-trifluoroethoxy)-difluoromethyl]-vinyl-cyclopropane-carboxylate.

4. A compound according to claim 1, which is 2,3,5,6-tetrafluoro-4-methyl-benzyl trans-2,2-dimethyl-3-[2-chloro-2-(2,2,2-trifluoroethyoxy)-difluoromethyl]-vinyl-cyclopropane-carboxylate.

5. A compound according to claim 1, which is pentafluoro-benzyl trans-2,2-dimethyl-3-[2-chloro-2-(2,2,3,3-tetrafluoropropoxy)-difluoromethyl]-vinyl-cyclopropane-carboxylate.

6. A compound according to claim 1, which is 2,3,5,6-tetrafluoro-4-methyl-benzyl trans-2,2-dimethyl-3-[2-chloro-2-(2,2,3,3-tetrafluoropropoxy)-difluoromethyl]-vinyl-cyclopropane-carboxylate.

7. A method for combatting infestations by noxious insects and acari consisting essentially in distributing throughout the infested area an insecticidally effective amount of one or more compounds according to claim 1, together with inert solid or liquid carriers.

8. An insecticidal or acaricidal composition containing an insecticidally or acaricidally effective amount of one or more compounds according to claim 1 as the active ingredient, together with inert solid or liquid carriers.

* * * * *